(12) United States Patent
Furuta (10) Patent No.: US 10,349,904 B2
(45) Date of Patent: Jul. 16, 2019

(54) POSITRON CT APPARATUS (71) Applicant: SHIMADZU CORPORATION, Kyoto (JP)

(72) Inventor: Masafumi Furuta, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 750 days.

(21) Appl. No.: 14/764,932

(22) PCT Filed: Jan. 21, 2014

(86) PCT No.: PCT/JP2014/051121
§ 371 (c)(1),
(2) Date: Jul. 30, 2015

(87) PCT Pub. No.: WO2014/119428
PCT Pub. Date: Aug. 7, 2014

(65) Prior Publication Data
US 2015/0366519 A1 Dec. 24, 2015

(30) Foreign Application Priority Data
Jan. 31, 2013 (JP) .................... 2013-017225

(51) Int. Cl.
A61B 6/03 (2006.01)
A61B 6/04 (2006.01)
(Continued)

(52) U.S. Cl.
CPC ............ *A61B 6/037* (2013.01); *A61B 6/0407* (2013.01); *A61B 6/102* (2013.01); *A61B 6/4057* (2013.01);
(Continued)

(58) Field of Classification Search
CPC ....... A61B 6/037; A61B 6/0407; A61B 6/102; A61B 6/4057; A61B 6/4266;
(Continued)

(56) References Cited

U.S. PATENT DOCUMENTS 8,452,381 B2   5/2013   Cora et al.

FOREIGN PATENT DOCUMENTS

FR   2697918 A1   5/1994
JP   11-285492 A   10/1999
(Continued)

OTHER PUBLICATIONS

Supplementary European Search Report EP Application No. 14 74 6255.0 dated Dec. 15, 2015.
(Continued)

*Primary Examiner* — Michael T Rozanski
(74) *Attorney, Agent, or Firm* — McDermott Will & Emery LLP (57) ABSTRACT

Two detector units and two holding arms are provided. The detector units are each disposed on a part of an arc of a circle surrounding a subject. The holding arms each disposed on the arc hold the detector units individually. The holding arms move independently along the circle surrounding the subject, thereby causing the detector units to move. Consequently, a first detector unit is held with a first holding arm entirely, and a second detector unit is held with a second holding arm entirely. This causes less swing of the detector units achieving a simple configuration.

8 Claims, 7 Drawing Sheets (51) Int. Cl.
   *A61B 6/00* (2006.01)
   *A61B 6/10* (2006.01)
   *G01T 1/29* (2006.01)
(52) U.S. Cl.
   CPC .......... *A61B 6/4266* (2013.01); *A61B 6/4275* (2013.01); *A61B 6/4405* (2013.01); *A61B 6/4441* (2013.01); *A61B 6/5205* (2013.01); *G01T 1/2985* (2013.01)
(58) Field of Classification Search
   CPC ... A61B 6/4275; A61B 6/4405; A61B 6/4441; A61B 6/5205; G01T 1/2985
   See application file for complete search history.

(56) References Cited

FOREIGN PATENT DOCUMENTS

| | | |
|---|---|---|
| JP | 2006-055518 A | 3/2006 |
| JP | 2007-263865 A | 10/2007 |
| JP | 2008-524574 A | 7/2008 |
| JP | 4650324 B2 | 3/2011 |

OTHER PUBLICATIONS

Office Action issued in corresponding Japanese Patent Application No. 2016-201859, dated Sep. 12, 2017 with English translation.
International Search Report PCT/JP2014/051121 dated Feb. 18, 2014 with English translation.
Written Opinion of the International Searching Authority PCT/JP2014/051121 dated Feb. 18, 2014.
A.J. Reader et al., "Fast accurate iterative reconstruction for low-statistics positron volume imaging", Phys. Med. Biol. 43, 1998, pp. 835-846.

POSITRON CT APPARATUS

This application is a U.S. National Stage application under 35 U.S.C. § 371, of International Application PCT/JP2014/051121 filed on Jan. 21, 2014, which was published as WO 2014/119428 on Aug. 7, 2014. PCT/JP2014/051121 claims priority to Japanese Patent Application No. 2013-017225 filed Jan. 31, 2013. The subject matter of each is incorporated herein by reference in entirety.

TECHNICAL FIELD

The present invention relates to a positron CT apparatus that detects radiation emitted from positron radiopharmaceutical administered to a subject and generates a distribution image of positrons as an image. More particularly, the present invention is directed to a technique of imaging a human body for a subject.

BACKGROUND ART

A positron CT apparatus, i.e., a PET (Positron Emission Tomography) apparatus reconstructs a tomographic image of a subject only upon simultaneous detection (i.e., coincidence counting) of two gamma-rays generated through annihilation of a positive electron (Positron) with a plurality of detectors. Specifically, the radiopharmaceutical containing positron-emitting radionuclide is administered to the subject. Then pair annihilation gamma-rays of 511 Kev emitted from the administered subject are detected with detectors each formed by groups of many detector elements (e.g., scintillators). Thereafter, when gamma-rays are detected with two detectors within a certain time period, the gamma-rays are detected "coincidently", and are counted as pair annihilation gamma-rays. Moreover, a line (LOR: Line Of Response) is identified that connects the two detectors that detect positions where the pair annihilation gamma-rays are generated. Then information on coincidence that is detected in such a manner is stored for reconstruction, whereby a positron-emitting radionuclide image (i.e., a tomographic image) is obtained.

In recent years, such an apparatus has a trend to conduct a diagnosis by superimposing the tomographic image obtained by the PET apparatus on a shape image obtained by another type of modality apparatus. Accordingly, the number of apparatus such as a PET/CT apparatus has increased in which a plurality of PET apparatus and modality apparatus accept a mount table (e.g., bed) supporting the subject placed thereon.

However, addition of a new modality apparatus to the existing modality apparatus is difficult in terms of constraint of the bed. As a result, new purchase of a plurality of PET apparatus or modality apparatus is required. Accordingly, the present Applicant has suggested another type of PET apparatus. See Japanese Patent No. 4650324. That is, the PET apparatus is configured such that detector units and holding arms holding the detector units are mounted on a transportable carriage, and the detector units are disposed so as to surround the bed.

With the PET apparatus, the bed of the existing modality apparatus (e.g., X-ray CT apparatus) is commonly used and the carriage is transported close to the modality apparatus. This allows arrangement of the detector units adjacent to the modality apparatus. Consequently, additional arrangement of the PET apparatus to the existing modality apparatus is performable without new purchase of a plurality of PET apparatus and modality apparatus.

Figure 11:
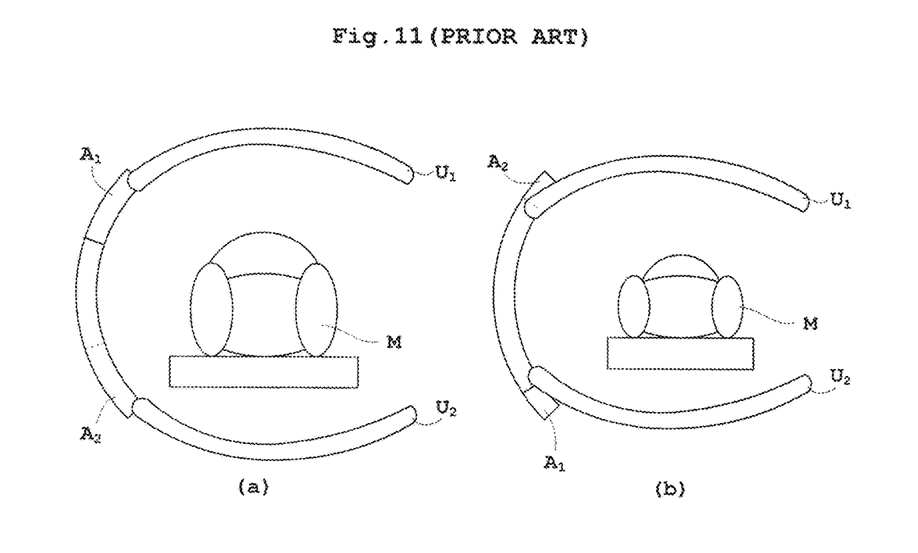
FIGS. 11(a) and 11(b) schematically illustrate a currently-used PET apparatus.

As illustrated in FIGS. 11(a) and 11(b), the PET apparatus includes two holding arms $A_1$, $A_2$ (a first C-shape arm, and a second C-shape arm) in an arc shape. The holding arms include at tips thereof detector units $U_1$, $U_2$ (a first gamma-ray detector, and second gamma-ray detector), respectively. The two holding arms $A_1$, $A_2$ move independently along a circle surrounding the subject M, thereby changing inclination angles of the detector units $U_1$, $U_2$ such that surfaces of the detector units $U_1$, $U_2$ into which gamma-rays enter face to each other across the subject M. Such a configuration allows variation in distance between the detector units $U_1$, $U_2$ depending on a size of the subject M while the inclination angles are changed as illustrated in FIGS. 11(a) and 11(b). This achieves radiography while the detector units $U_1$, $U_2$ face to each other.

[Patent Literature 1] Japanese Patent No. 4650324

SUMMARY OF INVENTION

Technical Problem

However, the apparatus having the configuration of FIGS. 11(a) and 11(b) possesses the following drawback. That is, as illustrated in FIGS. 11(a) and 11(b), the detector units $U_1$, $U_2$ are mounted on the tips of the holding arms $A_1$, $A_2$, respectively. In other words, the detector units $U_1$, $U_2$ are cantilevered. As a result, the detector units $U_1$, $U_2$ are likely to swing. Moreover, a mechanism is required that changes and controls the inclination angles. This causes a complicated configuration.

The present invention has been made regarding the state of the art noted above, and its object is to provide a positron CT apparatus with detector units unlikely to swing and thus achieves a simple configuration.

Solution to Problem

The present invention adopts the following construction for overcoming the above drawback. One embodiment of the present invention discloses a positron CT apparatus that performs radiography by detecting radiation emitted from positron radiopharmaceutical administered to a subject. The positron CT apparatus includes a plurality of detector units each disposed on a part of an arc of a circle surrounding the subject, and a plurality of holding arms each disposed on the arc and holding the detector units individually. The holding arms moves along the circle surrounding the subject independently, thereby causing the detector units to move.

Operation and Effect

With the embodiment of the positron CT apparatus, a plurality of detector units and a plurality of holding arms are provided. The detector units are each disposed on a part of the arc of the circle surrounding the subject. The holding arms each disposed on the arc hold the detector units individually. Here, the number of detector units is not necessarily equal to that of holding arms. The holding arms moves independently along the circle surrounding the subject, thereby causing the detector units to move. The detector units are each disposed on the arc, and the holding arms are also each disposed on the arc. Accordingly, the detector units are entirely held along the holding arms.

Consequently, the detector units are not cantilevered, causing a stable hold of the detector units. This results in less swing of the detector units. Moreover, the detector units are each disposed on the arc surrounding the subject. Accordingly, there is no need for a mechanism of changing and controlling inclination angles. This achieves a simple configuration.

Moreover, the detector units are disposed individually depending on a focused imaging area. This can produce another effect of enlarging a stereo angle surrounding the imaging area.

Moreover, it is preferable that the positron CT apparatus further includes a distance changing mechanism changing a distance between the adjacent detector units by moving the detector units and the holding arms in one direction. Especially, the distance changing mechanism reduces the distance between the adjacent detector units. This allows a more enlarged stereo angle surrounding the subject. Moreover, reduction in distance between the adjacent detector units causes the detector units to be close to the subject, achieving enhanced sensitivity of the detectors.

Moreover, it is preferable that an anti-collision mechanism is provided that prevents collision of the detector units with the holding arms caused by operation of the distance changing mechanism. For instance, when two detector units and two holding arms are provided, it is assumed that a first holding arm holds a first detector unit, and a second holding arm holds a second detector unit. The distance changing mechanism moves the detector units and the holding arms for changing a distances between the detector units. This may cause collision of the first holding arm with the second detector unit, or collision of the second holding arm with the first detector unit. Accordingly, the anti-collision mechanism is provided that prevents the collision of the detector unit with the holding arm caused by the operation of the distance changing mechanism. The mechanism can prevent the collision from occurring. Here, the anti-collision mechanism may be formed by a mechanical mechanism, a mechanism that electrically controls positions, or a mechanism in combination of the above mechanisms.

As mentioned above, one embodiment of the positron CT apparatus according to the present invention is configured such that the detector units and the holding arms are attached to the transportable carriage, and the detector units surround a mount table supporting the subject placed thereon. Such a configuration allows movement of the detector units and incorporation of the transportable the carriage. Consequently, the positron CT apparatus can image the subject placed on the mount table (e.g., bed) of the existing apparatus.

Advantageous Effects of Invention

With the embodiment of the positron CT apparatus, a plurality of detector units and a plurality of holding arms are provided. The detector units are each disposed on a part of the arc of the circle surrounding the subject. The holding arms each disposed on the arc hold the detector units individually. The holding arms move independently along the circle surrounding the subject, thereby causing the detector units to move. This causes less swing of the detector units, achieving a simple configuration.

DESCRIPTION OF EMBODIMENTS

Figure 1:
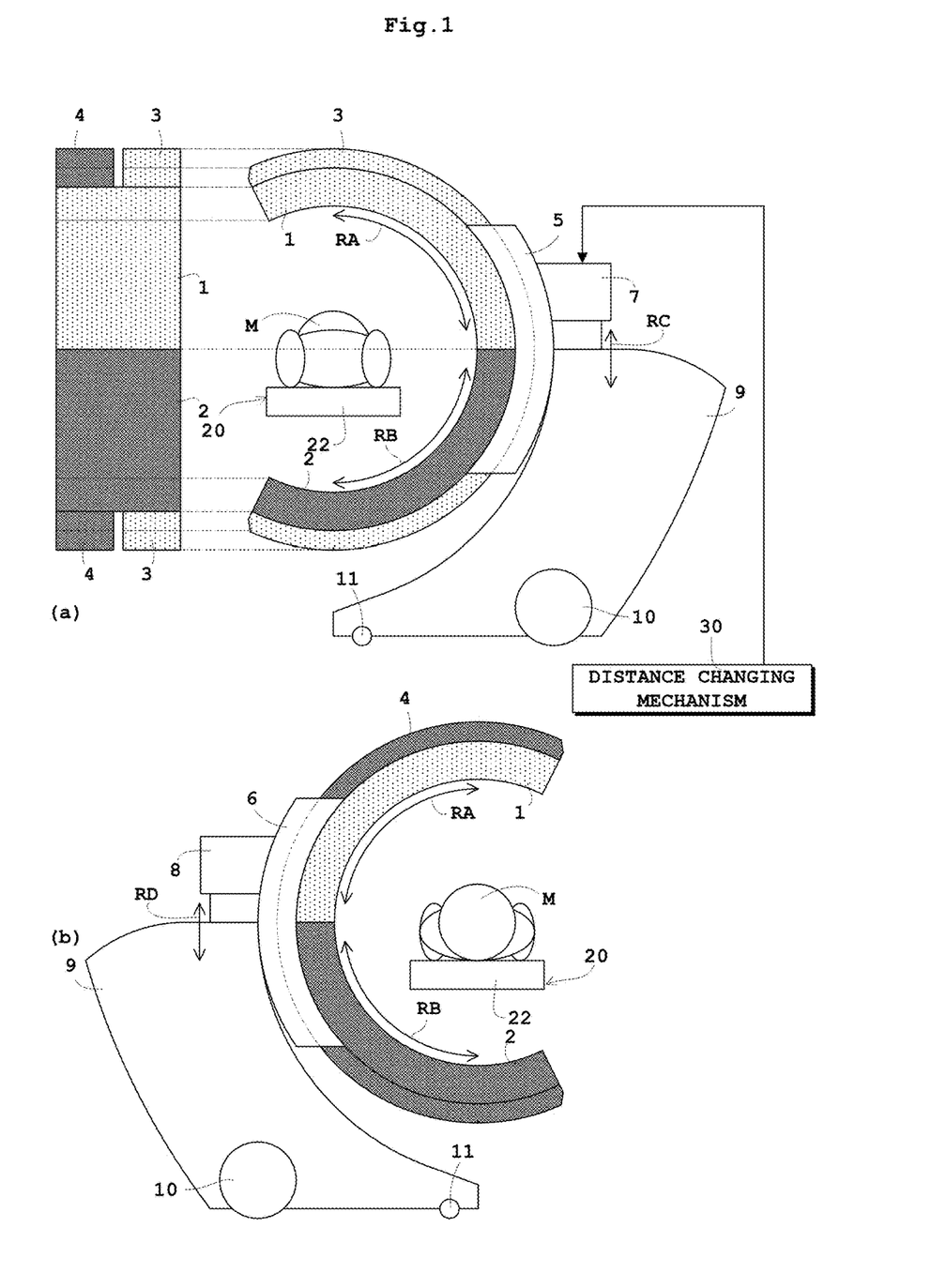
FIGS. 1(a) and 1(b) are schematic side views of a PET (Positron Emission Tomography) apparatus and a schematic front view of detector units and holding arms according to one embodiment of the present invention.
Figure 2:
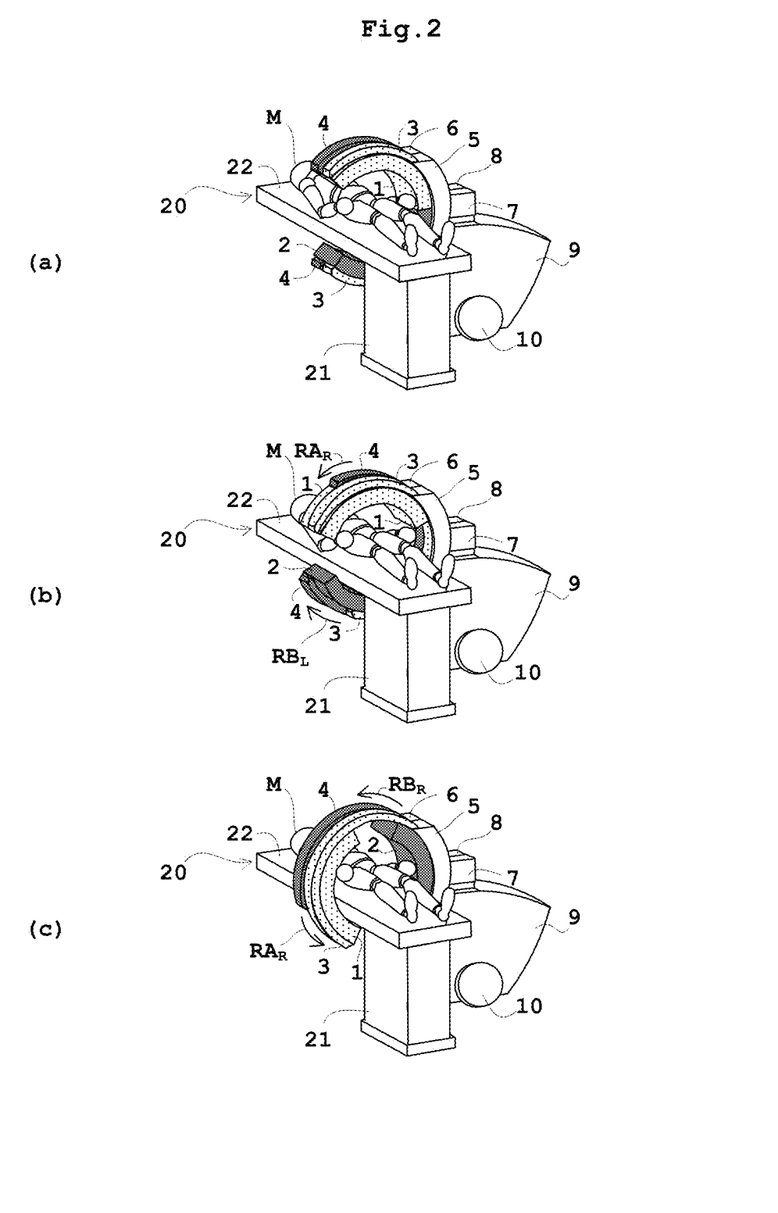
FIGS. 2(a), 2(b), and 2(c) are schematic perspective views of the PET apparatus according to the embodiment.

The following describes embodiments of the present invention with reference to drawings. FIGS. 1(a) and 1(b) are a schematic side view of a PET (Positron Emission Tomography) apparatus and a schematic front view of detector units and holding arms according to one embodiment of the present invention. FIGS. 2(a) to 2(c) are each a schematic perspective view of the PET apparatus according to the embodiment. Note that FIG. 1(b) is a side view of the PET apparatus seen reversely of FIG. 1(a), i.e., a side view seen from the head of a subject M.

As illustrated in FIGS. 1(a), 1(b), 2(a), 2(b), and 2(c), the PET apparatus according to the present embodiment includes two detector units 1, 2, and two holding arms 3, 4. The detector units 1, 2 are each disposed on a part of an arc of a circle surrounding the subject M. Similarly, the holding arms 3, 4 are each disposed on a part of the arc. Here, the holding arm 3 holds the detector unit 1. The holding arm 4 holds the detector unit 2. The detector units 1, 2 correspond to the detector units in the present invention. The holding arms 3, 4 correspond to the holding arms in the present invention.

The PET apparatus further includes two arm holders 5, 6, two lifting members 7, 8, and a transportable carriage 9. The arm holders 5, 6 hold the holding arms 3, 4, respectively. The holding arm 3 is slidable relative to the arm holder 5 in a direction of arrow RA (circumferential direction). The holding arm 4 is slidable relative to the arm holder 6 in a direction of arrow RB (circumferential direction). The carriage 9 corresponds to the carriage in the present invention.

The above configuration of the holding arms 3, 4 causes independent movement of the holding arms 3, 4 along the circle surrounding the subject M. In association with the movement of the holding arm 3, the detector unit 1 held on the holding arm 3 is moved in the same direction of arrow RA (circumferential direction). Moreover, in association with the movement of the holding arm 4, the detector unit 2 held on the holding arm 4 is moved in the same direction of arrow RB (circumferential direction).

As mentioned above, independent movement of the holding arms 3, 4 along the circle surrounding the subject M causes the detector units 1, 2 to move. Moreover, combination of the detector unit 1 and the holding arm 3 as well as combination of the detector unit 2 and the holding arm 4 are independently moved. Accordingly, in the drawing, the combination of the detector unit 1 and the holding arm 3 is denoted by dotted hatching, and the combination of the detector unit 2 and the holding arm 4 is denoted by dark gray fills for convenience.

The lifting members 7, 8 hold the arm holders 5, 6, respectively. The lifting member 7 is vertically movable relative to the carriage 9 in a direction of arrow RC (vertical direction, see FIG. 1(*a*)). The lifting member 8 is vertically movable relative to the carriage 9 in a direction of arrow RD (vertical direction, see FIG. 1(*b*)).

Such a configuration of the lifting members 7, 8 mentioned above causes the arm holders 5, 6 to move independently in the vertical direction. In association with the movement of the lifting member 7, the arm holder 5 held on the lifting member 7 is moved in the direction of arrow RC (vertical direction). In addition, the holding arm 3 held on the arm holder 5 as well as the detector unit 1 held on the holding arm 3 are also moved in the direction of arrow RC (vertical direction). Moreover, in association with the movement of the lifting member 8, the arm holder 6 held on the lifting member 8 is moved in the same direction of arrow RD (vertical direction). In addition, the holding arm 4 held on the arm holder 6 as well as the detector unit 2 held on the holding arm 4 are also moved in the same direction of arrow RD (vertical direction).

The carriage 9 includes on a bottom thereof a rear wheel 10 and a front wheel 11. These wheels are moved on the floor, whereby the carriage 9 is transportable. The front wheel 11 is connected to a motor (not shown) via a driving shaft (not shown). The motor drives, and correspondingly the front wheel 11 drives. An operator rotates the rear wheel 10 by pushing and pulling the carriage 9 at a rear side thereof in any directions. This allows movement of the carriage 9 on the floor in any directions. Consequently, transporting the carriage 9 to a side close to an existing apparatus (e.g., a modality apparatus such as an X-ray CT apparatus) allows arrangement of the detector units 1, 2 adjacent to the existing apparatus.

The existing apparatus is provided with a bed 20 external to the PET apparatus. The bed 20 includes a base 21 (not shown in FIGS. 1(*a*) and 1(*b*)), and a top board 22. The base 21 is disposed on the floor. The base 21 is extendable vertically, thereby changing a level of the top board 22 held on the base 21. The top board 22 supports the subject M placed thereon. The top board 22 is movable horizontally relative to the base 21.

The PET apparatus further includes a distance changing mechanism 30 (only shown in FIG. 1(*a*)). The distance changing mechanism 30 moves distance units 1, 2 and the holding arms 3, 4 in one direction, thereby changing a distance between the detector units 1, 2. In FIG. 1(*a*), the distance changing mechanism 30 is only connected to the lifting member 7. However, in the present embodiment, the distance changing mechanism 30 is actually connected also to the arm holders 5, 6 and the lifting member 8. The distance changing mechanism 30 is formed by a motor, a driving shaft, a gear, and a rack (each of them not shown). The distance changing mechanism 30 corresponds to the distance changing mechanism in the present invention.

In order to slide the holding arm 3 relative to the arm holder 5 in the direction of arrow RA (circumferential direction) with the distance changing mechanism 30, the motor, the driving shaft, and the gear are attached to the arm holder 5, and an arc-shaped rack is attached to the holding arm 3. Driving the motor causes the gear to drive via the driving shaft, and accordingly, causes the arc-shaped rack engaged with the gear to drive, thereby causing the holding arm 3 to slide relative to the arm holder 5 in the direction of arrow RA (circumferential direction). The same is applied for slide of the holding arm 4 relative to the arm holder 6 in the direction of arrow RB (circumferential direction) with the distance changing mechanism 30.

The distance changing mechanism 30 does not necessarily have such a configuration as above. For instance, the distance changing mechanism 30 is formed by a motor, a driving shaft, a gear, and a belt. The belt winds the holding arm 3. Driving the motor causes the gear to drive via a driving shaft. Winding of the belt engaged with the gear causes the holding arm 3 to slide relative to the arm holder 5 in the direction of arrow RA (circumferential direction). Such a configuration may be adopted.

In order to move the lifting member 7 relative to the carriage 9 vertically in the direction of arrow RC (vertical direction) with the distance changing mechanism 30, the motor, the driving shaft, and the gear are attached to the carriage 9, and a flat rack is attached to the lifting member 7. Driving the motor causes the gear to drive via the driving shaft, and accordingly causes the flat rack engaged with the gear to drive, thereby causing the lifting member 7 to move vertically relative to the carriage 9 in the direction of arrow RC (vertical direction). The same is applied for movement of the lifting member 8 vertically relative to the carriage 9 in the direction of arrow RD (vertical direction) with the distance changing mechanism 30.

The distance changing mechanism 30 does not necessarily have such a configuration as above. For instance, the distance changing mechanism 30 is formed by a motor, a driving shaft, a screw shaft, and a guide member. The lifting member 7 is slidably attached to the guide member. Driving the motor causes the screw shaft to rotate via the driving shaft. Rotation of the screw shaft causes the lifting member 7 to move vertically relative to the guide member in the direction of arrow RC (vertical direction), thereby causing the lifting member 7 to move vertically relative to the carriage 9 in the direction of arrow RC direction (vertical direction). Such a configuration may be adopted.

As noted above, the distance changing mechanism 30 causes the holding arms 3, 4 to slide in the circumferential direction relative to the arm holders 5, 6, and causes the lifting members 7, 8 to move vertically relative to the carriage 9. Moreover, the distance changing mechanism 30 causes the arm holders 5, 6 and the holding arms 3, 4 to move vertically. This allows movement of the holding arms 3, 4 in one direction (circumferential direction or vertical direction). Accordingly, the distance between the detector units 1, 2 is changed.

Scintillator blocks (not shown in FIGS. 1(*a*), 1(*b*), 2(*a*), 2(*b*), and 2(*c*)) of the gamma-ray detectors 1*a*, 2*a* (see FIGS. 5 and 6) convert gamma-rays into light. The gamma-rays are generated from the subject M to which the radiopharmaceutical is administered. Then photomultipliers (PMT: Photo Multiplier Tube) (not shown in FIGS. 1(*a*), 1(*b*), 2(*a*), 2(*b*), and 2(*c*)) in the gamma-ray detectors 1*a*, 2*a* multiply and convert the converted light into electric signals. The electric signals are transmitted to a coincidence circuit (not shown) as image information (pixel values).

Specifically, when the radiopharmaceutical is administered to the subject M, a positron of a positron-emission type RI (radioactive isotope) annihilates to generate two gamma-ray beams. The coincidence circuit checks positions of the scintillator blocks and an incidence timing of the gamma-ray beams. Only when the gamma-ray beams coincidently enter into two scintillator blocks facing to each other across the subject M, it is determined that the transmitted image information is valid data. When the gamma-ray beam enters into only one of the scintillator blocks, the coincidence circuit is invalid. That is, the coincidence circuit detects coincident observation of the gamma-ray beams in the two gamma-ray detectors 1a, 2a in accordance with the electric signals.

The image information transmitted to the coincidence circuit is determined as projection data. The projection data is reconstructed to generate a tomographic image (RI distribution image).

Figure 3:
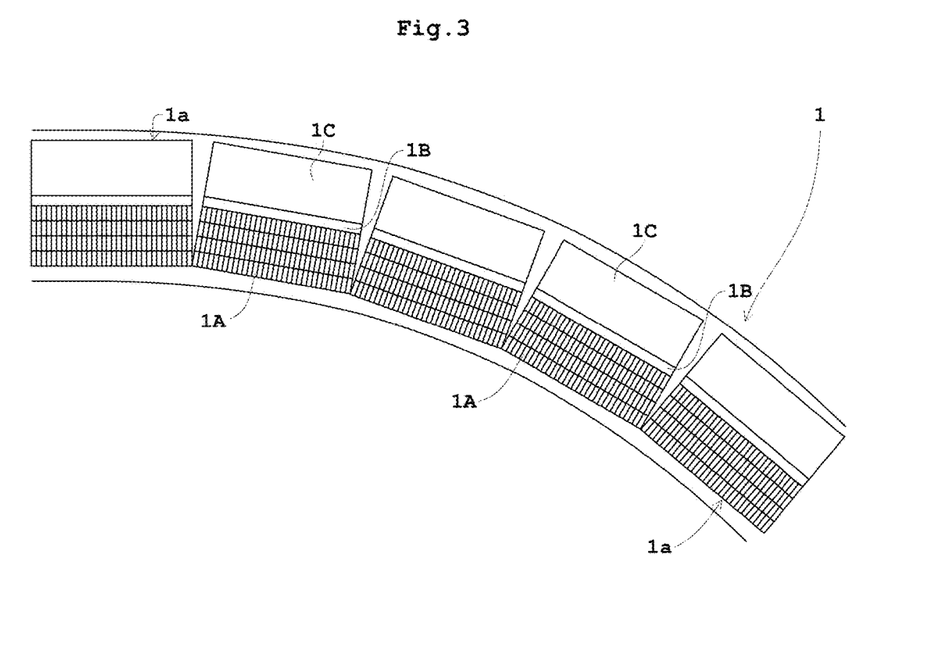
FIG. 3 schematically illustrates gamma-ray detectors in the detector unit.
Figure 4:
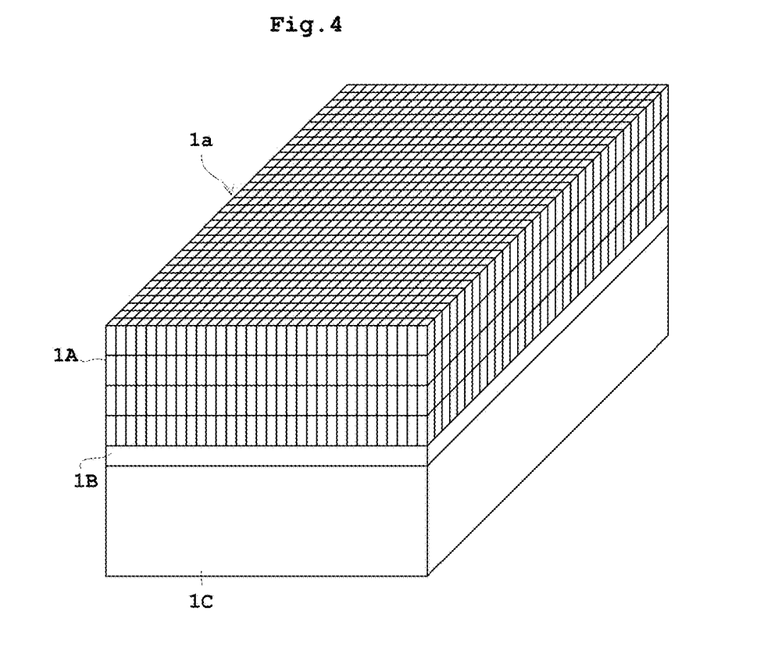
FIG. 4 schematically illustrates one of the gamma-ray detectors.

The following describes a concrete configuration of the detector units 1, 2 with reference to FIGS. 3 and 4. FIG. 3 schematically illustrates gamma-ray detectors in the detector unit. FIG. 4 is a schematic perspective view of one of the gamma-ray detectors. In FIGS. 3 and 4, the detector unit 1 is representatively illustrated. Since the detector unit 2 has the same configuration as that of the detector unit 1, the description thereof is to be omitted. In addition, a DOI detector is described as one example of the gamma-ray detector that allows discrimination of a position in a depth direction (DOI: Depth of Interaction) where interaction occurs.

As illustrated in FIG. 3, a plurality of gamma-ray detectors 1a is unitized in arc to form a detector unit 1. As illustrated in FIGS. 3 and 4, the gamma-ray detector 1a includes a scintillator block 1A, a light guide 1B optically coupled to the scintillator block 1A, and a photomultiplier 1C (hereinafter, simply abbreviated to "PMT") optically coupled to the light guide 1B. The scintillator block 1A is formed by scintillator elements. The scintillator elements glow in association with incident gamma-rays, thereby converting the gamma-rays into light. With the conversion, the scintillator elements detect gamma-rays. The light glowing in the scintillator elements diffuses sufficiently in the scintillator block 1A, and the light enters into a PMT 1C through the light guide 1B. The PMT 1C multiplies and converts the light in the scintillator block 1A into an electric signal. The electric signal is transmitted to the coincidence circuit (not shown) as the image information (pixel value) mentioned above.

As illustrated in FIG. 4, the gamma-ray detector 1a is composed of scintillator elements disposed three-dimensionally. Accordingly, the gamma-ray detector 1a is a DOI detector formed by a plurality of layers in the depth direction. FIGS. 3 and 4 each illustrate a four-layered DOI detector. However, the number of layers is not particularly limited as long as the number is plural. Moreover, the gamma-ray detector is not necessarily a DOI detector. Alternatively, the gamma-ray detector may be formed by only one-layered scintillator elements.

As mentioned above, the distance changing mechanism 30 (see FIGS. 1(a) and 1(b)) changes the distance between the detector units 1, 2. Accordingly, a relative position and a relative direction of the gamma-ray detectors 1a, 2a (as for a gamma-ray detector 2a of the detector unit 2, see FIGS. 5 and 6) vary constantly. Radiography is performed while the detector units 1, 2 face to each other in the vertical direction (see FIG. 2(b)), or in the horizontal direction (see FIG. 2(c)), or while the detector units 1, 2 approach the subject M (see FIG. 7(b)) depending on an imaging attitude or a size of the subject M. This causes an increased dose of gamma-rays detected in the gamma-ray detectors 1a, 2a, achieving enhanced gamma-ray sensitivity for detection by the gamma-ray detectors 1a, 2a. Consequently, with the present embodiment, radiography also proceeds while the position and direction of the gamma-ray detectors 1a, 2a vary relative to a mechanical origin of the apparatus.

Figure 5:
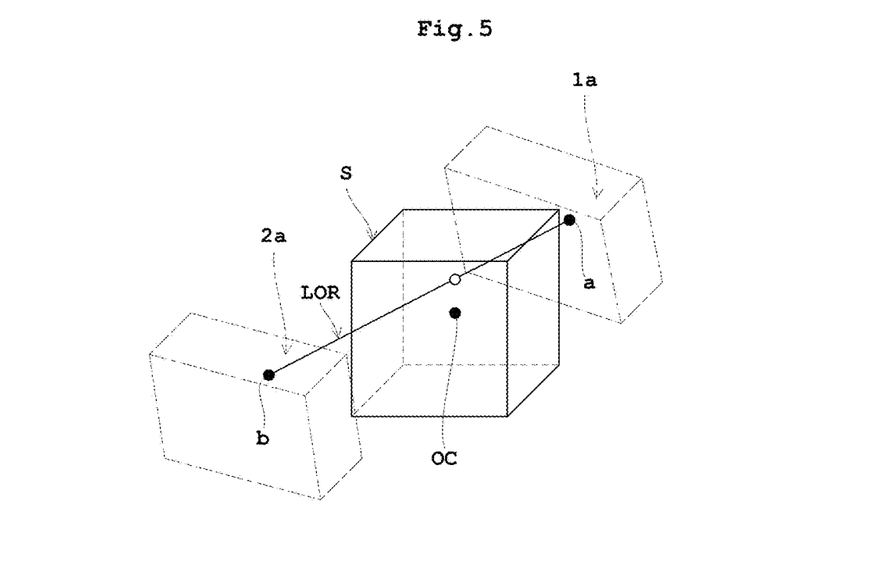
FIG. 5 is a schematic view of a positional relationship between the gamma-ray detectors and an image reconstruction area.
Figure 6:
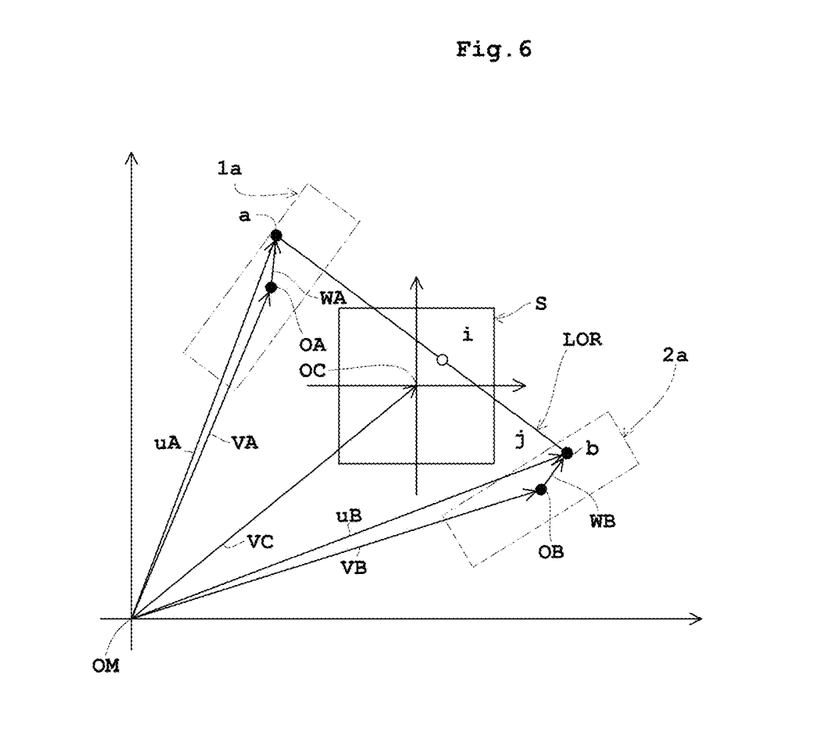
FIG. 6 is a graph illustrating a coordinate system of the gamma-ray detectors and the image reconstruction area.

The following describes a reconstruction algorithm with reference to FIGS. 5 and 6 upon variation in position and direction of the gamma-ray detectors 1a, 2a relative to the mechanical origin of the apparatus. FIG. 5 is a schematic view illustrating a positional relationship of both the gamma-ray detectors and an image reconstruction area. FIG. 6 is a graph illustrating coordinate systems of the both gamma-ray detectors and the image reconstruction area.

As illustrated in FIGS. 5 and 6, the gamma-ray detectors 1a, 2a are assembles of minute scintillators a, b, respectively. An image reconstruction area S having the center coordinate OC is disposed between the gamma-ray detectors 1a, 2a. The center coordinate OC is specified by a vector VC starting from a mechanical origin OM of the apparatus. Vectors VA, VB extending from the mechanical origin OM of the apparatus to the center coordinates OA, OB of the gamma-ray detectors 1a, 2a, respectively, are determined in accordance with position data of the gamma-ray detectors 1a, 2a detected by a position sensor (not shown) and rotation angle data of the gamma-ray detectors 1a, 2a detected with an angle sensor (not shown).

Consequently, when such phenomenon (hereinafter, abbreviated to "event" where appropriate) occurs as gamma-rays emitted from the subject M are coincidently counted, vectors uA, uB extending from the mechanical origin OM of the apparatus to scintillator elements a, b, respectively, having detected gamma-rays coincidently are given by the following Expressions (1) and (2):

$$uA = VA + WA \quad (1)$$

$$uB = VB + WB \quad (2)$$

Moreover, when the phenomenon (event) occurs that the gamma-rays emitted from the subject M are coincidently counted, address pair data of the scintillator elements a, b having detected the gamma-rays, and address pair data of the vectors uA, uB of the scintillator elements a, b having detected the gamma-rays is collected and stored for every event as list mode data. On the other hand, a line LOR (Line Of Response) connecting the scintillator elements a, b having detected the gamma-rays coincidently is determined for every event from the address pair data of the vectors uA, uB that is collected and stored as the list mode data. Here, positron-emitting radionuclide lies on the line LOR.

The vector uA is determined from information on the position and direction of the gamma-ray detectors 1a, 2a stored as the list mode data and the following Expression (3). Here, the data on the position and the direction of the gamma-ray detectors 1a, 2a may be stored as tag information only when the position and the direction vary.

$$uA = R_X \cdot R_Y \cdot R_Z \cdot WA \quad (3)$$

where $R_X$, $R_Y$, and $R_Z$ denote rotation of the gamma-ray detectors 1a, 2a about X-, Y-, and Z-axes, respectively, the axes being orthogonal to one another with reference to the mechanical origin OM of the apparatus, and T denotes a position in directions of the X-, Y-, and Z-axes (i.e., VA). Moreover, the vector uB is determinable in the same manner as that for the vector uA.

Mathematical Formula 1

$$R_X = \begin{bmatrix} 1 & 0 & 0 & 0 \\ 0 & \cos\alpha & \sin\alpha & 0 \\ 0 & -\sin\alpha & \cos\alpha & 0 \\ 0 & 0 & 0 & 1 \end{bmatrix}, R_Y = \begin{bmatrix} \cos\beta & 0 & -\sin\beta & 0 \\ 0 & 1 & 0 & 0 \\ \sin\beta & 0 & \cos\beta & 0 \\ 0 & 0 & 0 & 1 \end{bmatrix},$$

$$R_Z = \begin{bmatrix} \cos\gamma & \sin\gamma & 0 & 0 \\ -\sin\gamma & \cos\gamma & 0 & 0 \\ 0 & 0 & 1 & 0 \\ 0 & 0 & 0 & 1 \end{bmatrix}, T = \begin{bmatrix} 1 & 0 & 0 & 0 \\ 0 & 1 & 0 & 0 \\ 0 & 0 & 1 & 0 \\ A & B & C & 1 \end{bmatrix},$$

As noted above, a list mode reconstruction algorithm of iterative approximation type is applicable to the determination of the line LOR (Line Of Response) connecting the scintillator elements a, b having detected the gamma-rays coincidently for every event. See, Non-Patent Literature Reader et al 1998 Phys. Med Bial. 43 835-846. The update expression for obtaining an image with the list mode reconstruction algorithm is as the following Expression (4). The update Expression (4) is repeatedly performed to calculate an RI distribution image (distribution image of positron).

Mathematical Formula 2

$$f_j^{k+1} = \frac{f_j^k}{\sum_{j=1}^{I} a_{ij}} \sum_{i=1}^{M} \frac{1}{\sum_{j=1}^{J} a_{ij} f_i^k} a_{ij} \qquad (4)$$

where $f_j^k$ denotes a pixel value of a pixel j upon k-th repeat, $a_{ij}$ denotes the probability that a gamma-ray from the pixel j is detected by an LORi, M denotes the determined number of events, and I denotes the total number of LOR under the present radiographic condition (gamma-ray detector arrangement). Here, the update expression applicable to the present embodiment and used for the image reconstruction algorithm is not limited to the Expression (4). The image reconstruction algorithm is a known method referred to as an "iterative approximation method", and thus the detailed description thereof is to be omitted.

Figure 7:
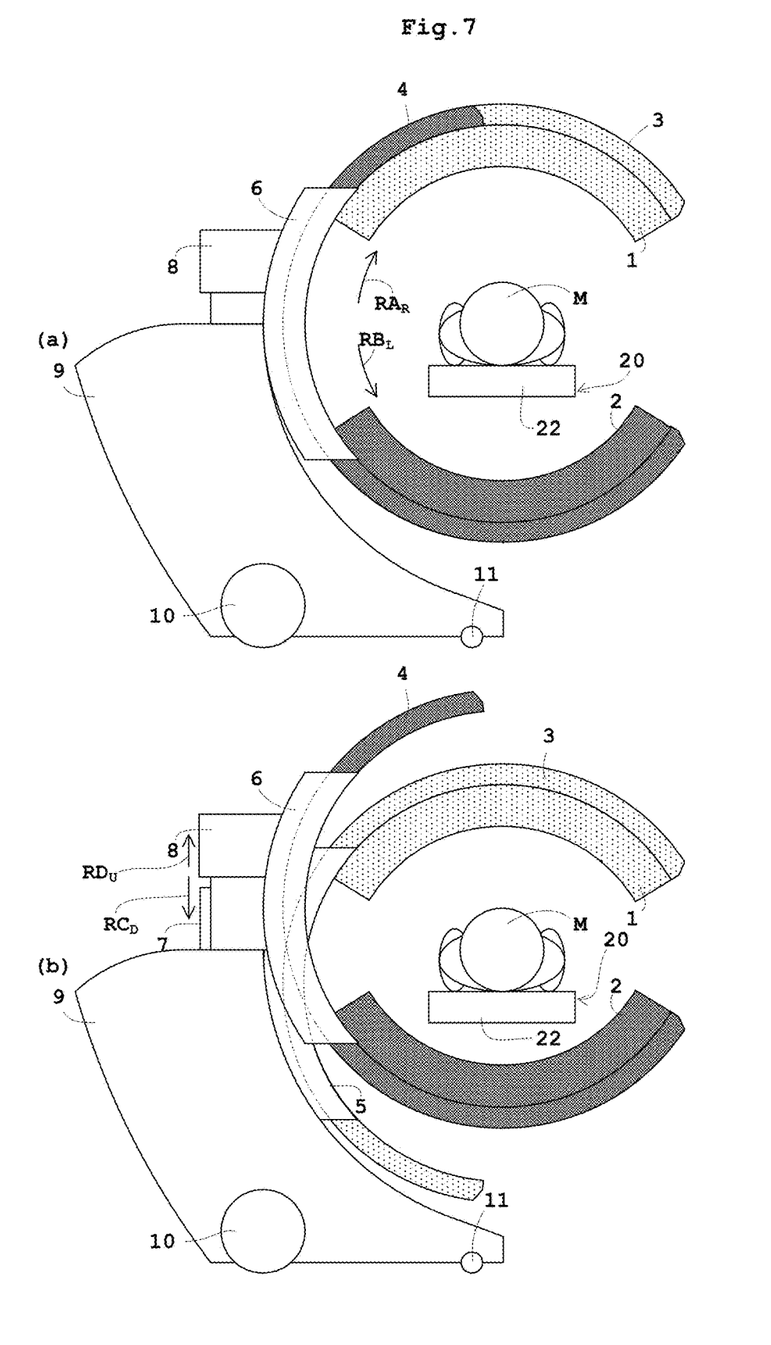
FIGS. 7(a) and 7(b) are schematic side views of an imaging mode by the PET apparatus.
Figure 8:
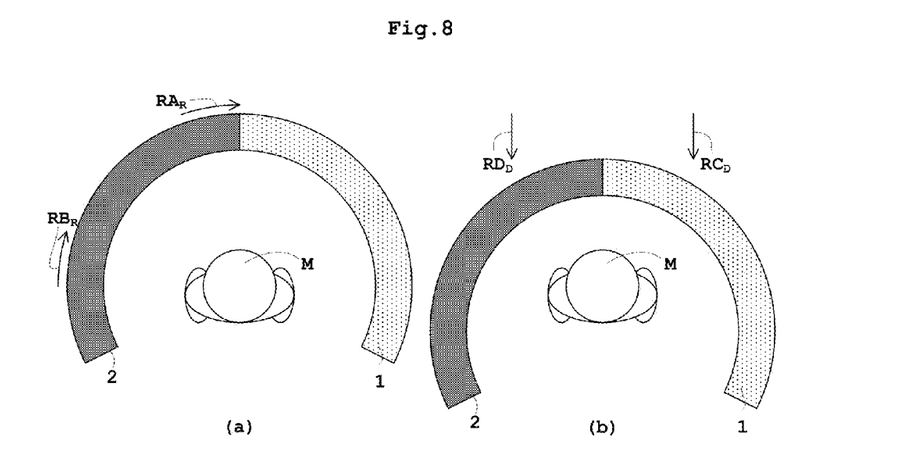
FIGS. 8(a) and 8(b) are schematic side views of another imaging mode by the PET apparatus that differs from the mode in FIGS. 7(a) and 7(b).
Figure 9:
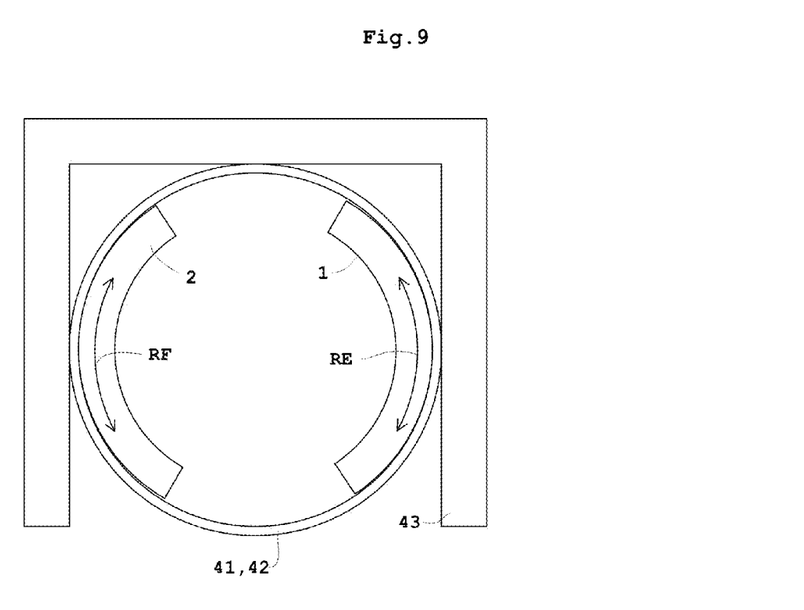
FIG. 9 is a schematic side view of a PET apparatus according to one modification of the present invention.

The following describes a concrete imaging mode of the PET apparatus with reference to FIGS. 7(a), 7(b), and 9 along with FIGS. 2(a), 2(b), and 2(c) mentioned above. FIGS. 7(a) and 7(b) are schematic side views of an imaging mode with the PET apparatus. FIGS. 8(a) and 8(b) are schematic side views of another imaging mode, different from that of FIGS. 7(a) and 7(b), with the PET apparatus. Similar to the side view of FIG. 1(b), FIGS. 7(a), 7(b), 8(a), and 8(b) are each a side view of the PET apparatus seen reversely of FIG. 1(a), i.e., a side view seen from the head of a subject M. Consequently, when the lifting members 7, 8 are disposed at the same level and thus the arm holders 5, 6 overlap one another completely, the arm holder 6 and the lifting member 8 remain hidden and only the arm holder 5 and the lifting member 7 are visible in FIG. 1(a), whereas the arm holder 5 and the lifting member 7 remain hidden and only the arm holder 6 and the lifting member 8 are visible in FIG. 7(a).

The following firstly describes an imaging mode illustrated in FIGS. 2(a) to 2(c). As illustrated in FIG. 2(a), the holding arms 3, 4 overlap one another completely, and ends of the detector units 1, 2 are adjacent to each other. From such a condition, the detector unit 1 is moved along with the holding arm 3 in the direction of arrow $RA_R$ (clockwise in the circumferential direction) in FIG. 2(b), and the detector unit 2 is moved along with the holding arm 4 in the direction of arrow $RB_L$ (counterclockwise in the circumferential direction). Then, the detector units 1, 2 are moved in the vertical direction across the subject M so as to face to each other. Here, the clockwise is a rotation direction seen from the subject M placed on his/her back on the top board 22, and the counterclockwise is a rotation direction seen from the subject M.

In contrast to this, as illustrated in FIG. 2(b), the detector units 1, 2 face to each other in the vertical direction. From such a condition, the detector unit 1 is moved along with the holding arm 3 in the direction of arrow $RA_R$ (clockwise in the circumferential direction) in FIG. 2(c), and the detector unit 2 is moved along with the holding arm 4 in the direction of arrow $RB_R$ (clockwise circumferential direction). Thereafter, the detector units 1, 2 face to each other horizontally on both sides of the subject M.

In the imaging mode illustrated in FIGS. 2(a) to 2(c), the holding arms 3, 4 slide in the direction of arrow RA (circumferential direction) or the direction of arrow RB (circumferential direction) at the same level without moving the lifting members 7, 8 vertically. Alternatively, as in the imaging mode in FIGS. 7(a) and 7(b), the lifting members 7, 8 are moved independently in the vertical direction to change the levels of the holding arms 3, 4. Such may be adopted.

The following describes an imaging mode illustrated in FIGS. 7(a) and 7(b). As illustrated in FIG. 2(a), the holding arms 3, 4 overlap one another completely, and ends of the detector units 1, 2 are adjacent to each other. From such a condition, the detector unit 1 is moved along with the holding arm 3 in the direction of arrow $RA_R$ (clockwise in the circumferential direction) in FIG. 7(a), and the detector unit 2 is moved along with the holding arm 4 in the direction of arrow $RB_L$ (counterclockwise circumferential direction). Then, similar to the mode in FIG. 2(b), the detector units 1, 2 are disposed vertically across the subject M so as to face to each other, as illustrated in FIG. 7(a).

Moreover, as illustrated in FIG. 7(a), the detector units 1, 2 face to each other vertically. From such a condition, the arm holder 5, the holding arm 3, and the detector unit 1 are moved downward along with the lifting member 7 in a direction of arrow $RC_D$ (downward in the vertical direction) in FIG. 7(b), and the arm holder 6, the holding arm 4, and the detector unit 2 are moved upward along with the lifting member 8 in a direction of arrow $RD_u$ (upward in the vertical direction). Thereafter, the detector units 1, 2 are disposed close to the subject M in the vertical direction.

The subject M is placed at the center of the detector units 1, 2 in FIGS. 1(a), 1(b), 2(a), 2(b), 2(c), 7(a), and 7(b). Alternatively, as illustrated in FIG. 8(b), the subject M may be placed close to the detector units 1, 2 radially. In an imaging mode illustrated in FIGS. 8(a) and 8(b), only shown are the detector units 1, 2 and the subject M, and thus other elements are not shown. As illustrated in FIG. 2(a), the ends of the detector units 1, 2 are adjacent to each other. From such a condition, the detector unit 1 is rotated by 90 degrees in the direction of arrow $RA_R$ (clockwise circumferential direction) in FIG. 8(a), and the detector unit 2 is rotated by 90 degrees in the direction of arrow $RB_R$ (clockwise in the circumferential direction). Thereafter, as illustrated in FIG. 8(a), the detector units 1, 2 are disposed above the subject M.

Moreover, as illustrated in FIG. 8(a), the detector units 1, 2 are disposed above the subject M. From such a condition, the detector unit 1 is moved downward in the direction of arrow $RC_D$ (downward in the vertical direction) in FIG. 8(*b*), and the detector unit 2 is moved downward in the direction of arrow $RD_D$ (downward in the vertical direction). Accordingly, the subject M is accessible to the detector units 1, 2 radially. Of course, the following may be adopted. That is, the detector units 1, 2 are not moved downward, but only the top board 22 (see FIGS. 1(*a*), 1(*b*), 2(*a*), 2(*b*), 2(*c*), 7(*a*), and 7(*b*)) is moved upward, whereby the subject M on the top board 22 is moved upward to be accessible to the detector units 1, 2 radially. In addition, the detector units 1, 2 are moved downward, and the top board 22 is moved upward, whereby the subject M is accessible to the detector units 1, 2 radially. Such may be adopted. The imaging mode in FIGS. 8(*a*) and 8(*b*) in which the detector units 1, 2 are disposed above the subject M is not limitative. The following modes are applicable. That is, the detector units 1, 2 are disposed below the subject M. The detector units 1, 2 are disposed on either a left side or a right side of the subject M. In such modes, the subject M may be accessible to the detector units 1, 2 radially in the same manner.

The PET apparatus of the present embodiment mentioned above includes a plurality of detector units (two detector units 1, 2 in the present embodiment) on a part of the arc of the circle surrounding the subject M, and a plurality of holding arms (two holding arms 3, 4 in the present embodiment) each disposed on the arc and holding the detector units 1, 2, respectively. The holding arms 3, 4 are moved independently along the circle surrounding the subject M, whereby the detector units 1, 2 are moved. The detector units 1, 2 are each disposed on the arc, and the holding arms 3, 4 are each disposed on the arc. Accordingly, the detector units 1, 2 are held entirely along the holding arms 3, 4. In the present embodiment, the detector unit 1 is entirely held along the holding arm 3, and the detector unit 2 is entirely held along the holding arm 4.

Consequently, the detector units 1, 2 are not cantilevered, causing a stable hold of the detector units 1, 2. This results in less swing of the detector units 1, 2. Moreover, the detector units 1, 2 are each disposed on the arc surrounding the subject M. Accordingly, there is no need for a mechanism of changing and controlling inclination angles.

Moreover, the detector units are disposed individually depending on a focused imaging area. This can produce another effect of enlarging a stereo angle surrounding the imaging area.

Moreover, it is preferable that the present embodiment further includes the distance changing mechanism 30 changing the distance between the adjacent detector units 1, 2, by moving the detector units 1, 2 and the holding arms 3, 4 in one direction (the circumferential direction or the vertical direction in the present embodiment). Especially, the distance changing mechanism 30 reduces the distance between the adjacent detector units 1, 2 (e.g., reduces the distance from that in the imaging mode in FIG. 7(*a*) to that in the imaging mode in FIG. 7(*b*)). This allows an enlarged stereo angle surrounding the subject M. Moreover, reduction in distance between the adjacent detector units 1, 2 causes approach of the detector units 1, 2 to the subject M, achieving enhanced sensitivity of the detectors.

In the present embodiment, the detector units 1, 2 and the holding arms 3, 4 are attached to the transportable carriage 9, and the detector units 1, 2 surround the mount table (bed 20 in the present embodiment) supporting the subject M placed thereon. Such a configuration allows movement of the detector units 1, 2 and incorporation of the transportable the carriage 9. Consequently, the PET apparatus can image the subject placed on the mount table (e.g., bed 20 in the present embodiment) of the existing apparatus (e.g., a modality apparatus such as an X-ray CT apparatus).

The present invention is not limited to the embodiment mentioned above, but may be modified as under.

(1) In the embodiment mentioned above, a human body has been described as one example of the subject. Alternatively, the present invention is applicable to a positron CT apparatus (PET apparatus) that images small animals (e.g., mice).

(2) In the embodiment mentioned above, the positron CT apparatus (PET apparatus) imaging a whole human body has been described. However, an imaging object is not limited to the whole body. That is, the present invention is applicable to a PET apparatus that images the head of a subject, or a mammography PET apparatus that images the breast of a subject.

(3) In the embodiment mentioned above, two detector units and two holding arms are provided. However, the number thereof is not limited to two as long as the number is plural. That is, three or more detector units and three or more holding arms may be adopted. Moreover, the number of detector units is not necessarily the same as that of holding arms as long as a plurality of detector units are each disposed on a part of the arc, and the holding arms are each disposed on the arc to move independently for moving the detector units.

(4) In the embodiment mentioned above, both the detector units and the holding arms are each disposed on a part of the arc. However, the holding arms may be arranged integratedly in a circular shape. For instance, as illustrated in FIG. 9, holding arms 41, 42 in a circular rail shape are disposed (one of the holding arms 41, 42 is disposed in front of the other of the holding arms 41, 42), and a gantry 43 holds the holding arms 41, 42. The holding arm 41 is moved in a direction of arrow RE (circumferential direction), and correspondingly the detector unit 1 held with the holding arm 41 is moved in the same direction of arrow RE (circumferential direction). Moreover, the holding arm 42 is moved in a direction of arrow RF (circumferential direction), and correspondingly the detector unit 2 held with the holding arm 42 is moved in the same direction of arrow RF (circumferential direction). Here, the detector units 1, 2 integrated in the circular shape are not movable. Consequently, the detector units 1, 2 are disposed in the same manner as that of the above embodiment, i.e., on a part of the arc.

(5) In the embodiment mentioned above, the detector units 1, 2 and the holding arms 3, 4 are moved in the circumferential direction or in the vertical direction for chancing the distance between the detector units 1, 2. However, the circumferential direction and the vertical direction are not limitative. The detector units and the holding arms may be moved in a horizontal direction. Alternatively, the detector units and the holding arms may be moved in a direction in combination of the circumferential direction or the vertical direction and the horizontal direction. In addition, the detector units and the holding arms may be moved radially with reference to the center of the circle surrounding the subject M.

(6) In the embodiment mentioned above, the detector units and the holding arms are attached to the transportable carriage, and the detector units surround the mount table of the existing apparatus. However, it is not always necessary to attach the detector units and the holding arms to the transportable carriage. Alternatively, the present invention is applicable to a PET apparatus having a base fixedly attached to the floor or the ceiling.

(7) In the embodiment mentioned above, a single PET apparatus has been described. Alternatively, the present invention is applicable to an apparatus in combination of the PET apparatus and another modality apparatus (e.g., X-ray CT apparatus).

(8) An anti-collision mechanism is preferably provided that prevents collision of the detector units with the holding arms caused by operation of the distance changing mechanism 30 (see FIG. 1(*a*)). As described in the embodiment above, when the two detector units and the two holding arms are provided, and a first holding arm 3 (see FIGS. 1(*a*), 1(*b*), 2(*a*), 2(*b*), 2(*c*), 7(*a*), and 7(*b*)) holds a first detector unit 1 (see FIGS. 1(*a*), 1(*b*), 2(*a*), 2(*b*), 2(*c*), 7(*a*), and 7(*b*)), and a second holding arm 4 (see FIGS. 1(*a*), 1(*b*), 2(*a*), 2(*b*), 2(*c*), 7(*a*), and 7(*b*)) holds a second detector unit 2 (see FIGS. 1(*a*), 1(*b*), 2(*a*), 2(*b*), 2(*c*), 7(*a*), and 7(*b*)), the distance changing mechanism 30 changing the distance between the detector units 1, 2 moves the detector units 1, 2 and the holding arms 3, 4 to cause possibility of collision of the holding arm 3 with the detector unit 2 or collision of the holding arm 4 with the detector unit 1. Especially, the holding arm 3 contacts the detector unit 2, and the holding arm 4 contacts detector unit 1. From such a condition, when the detector unit 1 and the holding arm 3 are moved upward or the detector unit 2 and the holding arm 4 moved downward, the holding arm 3 collides against the detector unit 2 and the holding arm 4 collides against the detector unit 1.

Figure 10:
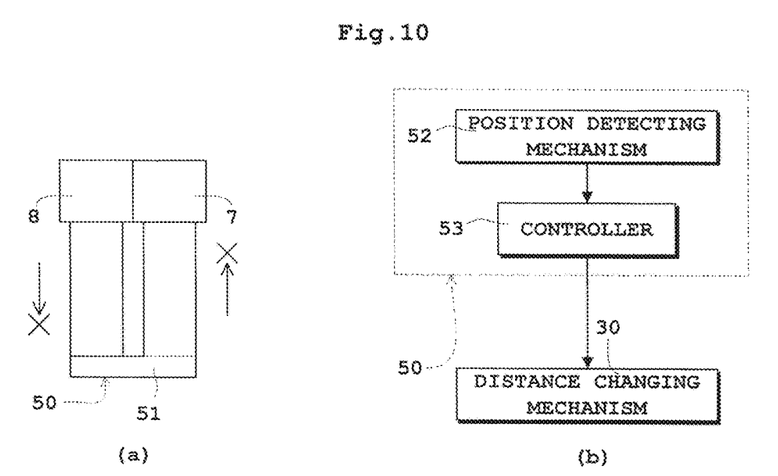
FIGS. 10(a) and 10(b) are schematic sectional views of an anti-collision mechanism.

Accordingly, an anti-collision mechanism 50 as illustrated in FIGS. 10(*a*) and 10(*b*) is provided to prevent collision of the detector unit with the holding arm caused by operation of the distance changing mechanism. Such a mechanism can prevent the collision from occurring. Here, the anti-collision mechanism 50 may be formed by a mechanical mechanism, a mechanism as illustrated in FIG. 10(*a*), a mechanism as illustrated in FIG. 10(*b*) that electrically controls positions, or a mechanism in combination of the above mechanisms. The anti-collision mechanism 50 corresponds to the anti-collision mechanism in the present invention.

As illustrated in FIG. 10(*a*), with the anti-collision mechanism 50 having a mechanical mechanism, the lifting member 7 includes a protrusion 51 on a lower end thereof. When the holding arm 3 (not shown in FIG. 10(*a*)) contacts the detector unit 2 (not shown in FIG. 10(*a*)), and the holding arm 4 (not shown in FIG. 10(*a*)) contacts the detector unit 1 (not shown in FIG. 10(*a*)), the lifting member 7 and the lifting member 8 are disposed at the same level. From such a condition, the lifting member 7 is moved upward or the lifting member 8 is moved downward, and correspondingly the detector unit 1 and the holding arm 3 are moved upward, or the detector unit 2 and the holding arm 4 are moved downward. As a result, the holding arm 3 collides against the detector unit 2, and the holding arm 4 collides against the detector unit 1. The above protrusion 51 provided so as to prevent the lifting member 7 above the lifting member 8 contacts the lifting member 8 immediately before the lifting member 7 is located above the lifting member 8. This allows mechanical stop of the lifting members 7, 8.

Moreover, as illustrated in FIG. 10(*b*), the anti-collision mechanism 50 performing positional control electrically includes a position detecting mechanism 52, such as a potentiometer. The position detecting mechanism 52 are attached to each of the detector units, the holding arms, or the lifting members. The positions of the detector units, the holding arms, or the lifting members are detected, and detection results by the position detecting mechanism 52 are transmitted to a controller 53 formed by a central processing unit (CPU) and the like. Then, when receiving the position results immediately before collision from the position detecting mechanism 52, the controller 53 controls the distance changing mechanism 30 to stop driving, whereby the collision is prevented from occurring.

REFERENCE SIGN LIST 1, 2 . . . detector unit
3, 4 . . . holding arm
9 . . . carriage
30 . . . distance changing mechanism
50 . . . anti-collision mechanism

The invention claimed is:

1. A positron CT apparatus performing radiography by detecting radiation emitted from positron radiopharmaceutical administered to a subject, the positron CT apparatus comprising:
   a plurality of detector units each disposed on a part of an arc of a circle surrounding the subject,
   a plurality of holding arms each disposed on the arc and holding the detector units individually, the holding arms moving along the circle surrounding the subject independently, thereby causing the detector units to move,
   arm holders holding the holding arms, individually, and
   elevators lifting the arm holders individually, wherein
   the elevators are configured to change the distance between the adjacent detector units by moving the arm holders in only a substantially vertical direction.

2. The positron CT apparatus according to claim 1, wherein
   the distance between the adjacent detector units changes by moving the holding arms in a circumferential direction.

3. The positron CT apparatus according to claim 2, wherein
   the holding arms move in the circumferential direction by sliding relative to the arm holders in the circumferential direction.

4. The positron CT apparatus according to claim 1, further comprising:
   an anti-collision mechanism preventing collision of the detector units with the holding arms, wherein
   the anti-collision mechanism is formed by a mechanical mechanism.

5. The positron CT apparatus according to claim 4, wherein
   when the number of detector units is two and the number of holding arms is two, and a first holding arm holds a first detector unit, and a second holding arm holds a second detector unit, the anti-collision mechanism prevents collision of the first holding arm with the second detector unit, or collision of the second holding arm with the first detector unit.

6. The positron CT apparatus according to claim 1, further comprising:
   an anti-collision mechanism preventing collision of the detector units with the holding arms, wherein
   the anti-collision mechanism is formed by a mechanism that electrically controls positions, and
   the anti-collision mechanism includes
   a position detector detecting positions of the detector units or the holding arms holding the detector units individually, and
   a controller controlling the anti-collision mechanism in accordance with a positional detection result by the position detector.

7. The positron CT apparatus according to claim 6, wherein when the number of detector units is two and the number of holding arms is two, and a first holding arm holds a first detector unit, and a second holding arm holds a second detector unit, the anti-collision mechanism prevents collision of the first holding arm with the second detector unit, or collision of the second holding arm with the first detector unit.

8. The positron CT apparatus according to claim 1, wherein the detector units and the holding arms are attached to a transportable carriage, and the detector units surround a mount table supporting the subject placed thereon.

* * * * *